United States Patent
Craeye

(10) Patent No.: US 12,116,282 B2
(45) Date of Patent: Oct. 15, 2024

(54) METHOD FOR THE DESULFURIZATION OF METHANE-CONTAINING GASES

(71) Applicant: DESOTEC NV, Roeselare (BE)

(72) Inventor: Johan Craeye, Izegem (BE)

(73) Assignee: DESOTEC NV, Roeselare (BE)

( * ) Notice: Subject to any disclaimer, the term of this patent is extended or adjusted under 35 U.S.C. 154(b) by 416 days.

(21) Appl. No.: 17/606,468

(22) PCT Filed: Dec. 9, 2019

(86) PCT No.: PCT/IB2019/060566
§ 371 (c)(1),
(2) Date: Oct. 26, 2021

(87) PCT Pub. No.: WO2020/222038
PCT Pub. Date: Nov. 5, 2020

(65) Prior Publication Data
US 2022/0194802 A1    Jun. 23, 2022

(30) Foreign Application Priority Data

May 2, 2019   (BE) .................................. 2019/5293

(51) Int. Cl.
| B01D 53/04 | (2006.01) |
| C01B 17/02 | (2006.01) |
| C01B 32/318 | (2017.01) |
| C10L 3/10 | (2006.01) |

(52) U.S. Cl.
CPC ............ *C01B 32/318* (2017.08); *B01D 53/04* (2013.01); *C01B 17/021* (2013.01); *C10L 3/103* (2013.01); *B01D 2253/102* (2013.01); *B01D 2256/245* (2013.01); *B01D 2257/30* (2013.01); *C10L 2290/542* (2013.01)

(58) Field of Classification Search
CPC ..... C01B 32/318; C01B 17/021; B01D 53/04; B01D 2253/102; B01D 2256/245; B01D 2257/30; C10L 3/103; C10L 2290/542; Y02E 50/30; C12M 47/18
USPC ......... 96/108; 95/135–137, 901; 423/244.01; 502/416
See application file for complete search history.

(56) References Cited

U.S. PATENT DOCUMENTS 9,579,626 B1 * 2/2017 Sesselmann ........... B01J 20/165
2023/0166235 A1 * 6/2023 Butterworth ........... A61G 17/06
                                                                    95/90

FOREIGN PATENT DOCUMENTS

| CN | 201865755 U | 6/2011 |
| CN | 103693643 A | * 4/2014 |
| JP | 2018089553 A | * 6/2018 |

OTHER PUBLICATIONS

Machine-generated English translation of JP 2018-089553A, published Jun. 14, 2018.*
Machine-generated English translation of CN 103693643 A, published Apr. 2, 2014.*
PCT International Search Report and Written Opinion dated Mar. 9, 2020 in connection with PCT International Patent Application No. PCT/IB2019/060566.
Russamee Sitthikhankaew et al: "Effect of KI and KOH Impregnations over Activated Carbon on H 2 S Adsorption Performance at Low and High Temperatures," Separation Science and Technology, vol. 49, No. 3, Feb. 11, 2014 (Feb. 11, 2014), pp. 354-366, XP055656301.
Nurul Noramelya Zulkefli et al: "Removal of hydrogen sulfide from a biogas mimic by using impregnated activated carbon adsorbent," PLOS One, vol. 14, No. 2, Feb. 1, 2019 (Feb. 1, 2019), e0211713, pp. 1-25, XP055656239.
Wan Asma Ibrahim et al: "Production of Activated Carbon from Industrial Bamboo Wastes Gasification View project Enzymes View project," Jul. 1, 2011 (Jul. 1, 2011), XP055656244, Retrieved from the Internet: URL:https://www.researchgate.net/profile/Rafidah_Jalil/publication/267827623_Production_of-Activated_Carbon_fromIndustrial_Bamboo_Wastes/links/545b2b560cf2c46f66439bf5/Production-of-Activated-Carbon-from-Industrial-Bamboo-Wastes.pdf.

* cited by examiner

*Primary Examiner* — Frank M Lawrence, Jr.
(74) *Attorney, Agent, or Firm* — Amster, Rothstein & Ebenstein LLP

(57) ABSTRACT

The invention relates to a method for the desulfurization of methane-containing gases by bamboo-based activated carbon. The method according to the invention is particularly suitable for the desulfurization of methane-containing gases such as biogas, landfill gas, mine gas, flue gas, marsh gas or natural gas with a view to further use of the gas or the sulfur extracted.

10 Claims, No Drawings

METHOD FOR THE DESULFURIZATION OF METHANE-CONTAINING GASES

CROSS-REFERENCE TO RELATED APPLICATIONS

This application is a U.S. national stage entry under 35 U.S.C. § 371 of PCT International Patent Application No. PCT/IB2019/060566, filed Dec. 9, 2019, which claims priority to Belgian Patent Application No. 2019/5293, filed May 2, 2019, the contents of each of which are incorporated herein by reference in their entirety.

FIELD OF THE INVENTION

The invention relates to a method for the desulfurization of methane-containing gases by bamboo-based activated carbon. The method according to the invention is particularly suitable for the desulfurization of methane-containing gases such as biogas, landfill gas, mine gas, flue gas, marsh gas or natural gas with a view to further use of the gas or the extracted sulfur.

BACKGROUND OF THE INVENTION

The use of methane-containing gases for the production of electricity or heat is ubiquitous in the present energy landscape. Gases used for these applications contain a high percentage of methane and it is important that they are obtained in as clean a form as possible for the aforementioned applications. However, these gases are obtained in a contaminated form from the existing sources and it is necessary to remove the impurities from these gases.

The methane-containing gases obtained initially comprise considerable amounts of sulfur. Besides the removal of water, oil, carbon dioxide and other byproducts, the removal of sulfur from the methane-containing gas is one of the most important purification processes. Sulfur occurs in methane-rich gases as hydrogen sulfide ($H_2S$) or volatile organic sulfur compounds (mercaptans, among others). The presence of sulfur gives rise to a putrid odor, and it is very harmful to inhale since it can cause asthma attacks, possibly even with lethal consequences. Furthermore, the presence of sulfur may also make the gas very corrosive, which means that it is totally unacceptable in gases intended for energy supply, as it would damage the equipment used. The sulfur present in the gas can possibly be utilized in one or other form and can be sold as a basic chemical for applications in fertilizer, plaster and vulcanized rubber and thus provide a source of revenue.

Various methane-containing gases such as biogas, landfill gas, mine gas, flue gas, marsh gas or natural gas form the basis for energy supply processes.

The use of methane-containing gases is encouraged on account of the favorable combustion properties of methane. In addition, methane is a greenhouse gas that is about 25 times stronger than $CO_2$ (carbon dioxide). However, methane-containing gases comprise contaminants, including sulfur-containing compounds, which on combustion are very harmful for people and the environment. Sulfur oxides are in fact an important component of air pollution and smog, and give rise to acid rain or acid deposits. The presence of sulfur in the atmosphere and water is thus a growing problem. Acidification has in various ways a negative influence on humans, animals, and the environment.

Carbon-containing adsorbents, and especially activated carbon, are used for desulfurization. This manner of desulfurization is characterized by a lower amount of reagents required for desulfurization and so also has a low cost price. In addition, the sulfur-containing products are thus recycled in the form of sulfuric acid, ammonium sulfate, sodium sulfite, bisulfite or sulfate, calcium sulfate and sulfur, and the technology is simple to carry out. There is also no problem of secondary pollution.

However, the regeneration of used activated carbon is still expensive and therefore cheaper and more efficient alternatives are sought, which contribute to ecological sustainability and offer advantages for future commercial applications.

SUMMARY OF THE INVENTION

The invention described herein relates to the use, a method and an installation in which bamboo-based activated carbon is used for purifying methane-containing gases. Bamboo-based activated carbon is capable of desulfurizing methane-containing gases, which leads to improved purity of the methane-containing gas. A consequence of desulfurization is that in subsequent processes the methane-containing gas is converted safely into electricity and/or heat in combined heat and power generation, or alternatively is further purified for injection into a natural gas network. The technology described is applicable to any methane-containing gas such as biogas, landfill gas, mine gas, flue gas, marsh gas or natural gas.

Accordingly the present invention provides a method for the desulfurization of methane-containing gases comprising contacting activated carbon with methane-containing gas, wherein the activated carbon is an activated carbon based on bamboo.

In particular, the method as described herein provides generation of the activated carbon from a composition consisting of at least 50 wt % of bamboo.

In particular, the method as described herein provides that the pores in the activated carbon, with which the methane-containing gas comes into contact, form an alkaline environment.

In particular, the method as described herein provides that the activated carbon contains at least one of the additional constituents: $H_2O$ (water), NaOH, $K_2CO_3$, KI, KOH, CaO, MgO, CuO, MnO.

In particular, the method as described herein provides that at least one of the additional constituents is present in the following amounts: 1.0 to 30.0% $H_2O$ (water); 1.0 to 30.0% NaOH; 1.0 to 15.0% $K_2CO_3$; 1.0 to 10.0% KI; 1.0 to 15.0% KOH; 1.0 to 10.0% CaO; 1.0 to 10.0% MgO; 1.0 to 10.0% CuO; and/or 1.0 to 10.0% MnO.

In particular, the method as described herein provides that the methane-containing gas is a biogas, landfill gas, mine gas, flue gas, marsh gas or natural gas.

In particular, the method as described herein provides that the methane-containing gas contains at least 10% methane, preferably at least 20% methane, preferably at least 40% methane, preferably at least 50% methane.

In particular, the method provides that the bamboo-based activated carbon has a pore distribution whose value is expressed with a minimum butane number of 20.

In particular, the method as described herein provides that the saturated sulfur capacity of the activated carbon is at least 50 wt % based on the fresh (initial, unladen) activated carbon.

In particular, the method as described herein provides that the activated carbon is also a reactivated carbon.

In particular, the method as described herein provides that the sulfur content of the gas is reduced by at least 99% using fresh bamboo-based activated carbon relative to untreated gas.

In a further aspect, the present invention provides the use of bamboo-based activated carbon for the desulfurization of methane-containing gases.

In a further aspect, an installation is provided, arranged for the desulfurization of methane-containing gases according to the method as described herein, comprising a filter that contains the activated carbon, wherein the filter accomplishes contact with methane-containing gas, wherein the activated carbon is an activated carbon based on bamboo.

DETAILED DESCRIPTION OF THE INVENTION

Before the present method, the present use and the present installation of the invention are described, it should be made clear that the present invention is not limited to specific systems and methods or combinations that are described, since said methods, installations and combinations may of course vary. It should also be made clear that the terminology that is used herein is not meant as being limiting, since the scope of the present invention is limited exclusively by the appended claims.

As used herein, the singular forms "the" and "a" encompass both the singular and plural references, unless the context clearly indicates otherwise.

The terms "comprising", "comprises" and "consisting of" are, as used herein, synonymous with "inclusive", "including" or "containing", "contains" and are inclusive or open-ended and do not exclude any additional, unstated members, components or steps. It will be clear that the terms "comprising", "comprises" and "consisting of" as used herein encompass the terms "consisting of" and "consists of".

The statement of numerical ranges with end points comprises all numbers and fractions that fall within said range, as well as the stated end points.

The term "about" or "approximately", as used herein when referring to a measurable value such as a parameter, an amount, a duration and the like, is meant to comprise variations of +/−10% or less, preferably +/−5% or less, more preferably +/−1% or less and even more preferably +/−0.1% or less than the 10 specified value, in so far as such variations are suitable for being made in the invention described. It should be made clear that the value to which the modifier "about" or "approximately" refers is itself also specific and is preferably described.

Although the terms "one or more" or "at least one", such as one or more members or at least one member of a group of members, are clear per se, by way of further explanation the terms comprise among other things a reference to one of said members or to any arbitrary two or more of said members, such as any arbitrary ≥3, ≥4, ≥5, ≥6 or ≥7, etc. of said members, and up to all said members.

All references that are cited in the present description are incorporated hereby by reference in their entirety. In particular, the teaching of all references specifically referred to herein is incorporated by reference.

Unless otherwise defined, all terms that are used when describing the technology, including technical and scientific terms, have the same meaning as is understood by someone with an average knowledge of the field to which this technology belongs. By way of further guidance, the definitions of the terms are included for better understanding of the teaching of the present technology.

Various aspects of the invention are defined in more detail in the following passages. Each aspect that is defined as such may be combined with any other aspect or any other aspects, unless the contrary is clearly stated. In particular, any feature that is indicated as being preferred or advantageous may be combined with any other feature or any other features that are stated to be preferred or advantageous.

Throughout this description, reference to "an embodiment" or "one embodiment" signifies that a specific feature, specific structure or property that is described in connection with the embodiment is incorporated in at least one embodiment of the present invention. Thus, appearances of the phrases "in an embodiment" or "in one embodiment" at different places in this description do not necessarily all refer to the same embodiment, but they might well. Moreover, the specific features, structures or properties may be combined in any suitable way in one or more embodiments, as would be clear to an expert in the field of study from this description. Although particular embodiments that are described herein comprise some features that are not included in other embodiments, but others are not, combinations of features of different embodiments are moreover intended to fall within the scope of the invention, and to form individual embodiments, as would be clear to experts in the field of study. For example, in the appended claims, each of the claimed embodiments may be used in any combination.

The following detailed description should consequently not be construed as being limiting, and the scope of the present invention is defined by the appended claims.

In a first aspect, the present technology relates to a method for the desulfurization of methane-containing gases making use of bamboo-based activated carbon.

Desulfurization is obtained by bringing the methane-containing gas into contact with the activated carbon. Concretely, desulfurization is obtained by adsorption and/or complete or partial oxidation of sulfur-containing molecules from the methane-containing gas by the activated carbon, wherein the activated carbon is used in powder form, granular form, extruded form, bead form, impregnated form, polymer coating form or woven form. Contamination of methane-containing gases is problematic and, in particular, sulfur compounds in methane-containing gases are problematic for the equipment through which the methane-containing gas is passed. The corrosive character of sulfur leads to functional and structural problems with the equipment. The inventors observed, unexpectedly, that bamboo-based activated carbon possesses various advantages relative to other forms of activated carbon for the desulfurization of methane-containing gases. Thus, bamboo-based activated carbon has a high mechanical strength, a high Brunauer, Emmett and Teller (BET) content indicative of the internal surface area of the activated carbon, and the correct pore distribution for the neutralization, oxidation and storage of the sulfur-containing components. In addition, the abundance of bamboo ensures quick and cheap supply, and in addition it is renewable as a raw material, and has a much better environmental impact relative to the more usual types of activated carbon based on fossil raw materials. This method includes the use of bamboo-based activated carbon regardless of the precise carbonization and activation protocol used for the generation thereof. The method described is applicable for gases for which the sulfur content is known at the start of the method, is based on an estimate, or is unknown.

In general, desulfurization is obtained by bringing the methane-containing gas into contact with the activated carbon once or several times, wherein the activated carbon in loose form is brought into contact with the methane-containing gas, or in a form wherein the activated carbon is surrounded by gas-permeable packaging or a gas-permeable membrane. Contact between the methane-containing gas and the bamboo activated membrane is characterized by incubation without movement of air, or by contact wherein the gas is led passively or actively at a constant or variable flow rate through a space that contains the bamboo-based activated carbon.

As used herein, the term "desulfurization" refers to the removal of sulfur-containing components or molecules from raw materials, intermediates or residual products, wherein the consequence of desulfurization is a reduction, decrease of the sulfur concentration relative to the starting material. The term "desulfurization" preferably refers to the removal of any sulfur-containing compound, not being limited to $H_2S$ (hydrogen sulfide) or $SO_2$ (sulfur dioxide). This has the result that the sulfur-containing molecule belongs but is not limited to the group of sulfides, thiols, disulfides, polysulfides, thioesters, sulfoxides, sulfones, thiosulfinates, sulfimides, sulfoximides, sulfonediimines, S-nitrosothiols, sulfur halides, thioketones, thioaldehydes, thiocarboxylates, thioamides, sulfuric acids, sulfonic acids or sulfuranes.

As used herein, the term "activated carbon" usually refers to a carbon-containing material consisting partially or largely of carbon. In particular, a material is meant that has undergone a thermal and/or chemical activating process and as a result contains a large number of pores, which dramatically increases the contact surface area of this material relative to unactivated material. This material is characterized by a high adsorption capacity of one or more substances. Activated carbon possesses a common definition with other currently used terms for this material such as "active carbon", "activated charcoal", "active charcoal" or "Norit".

As used herein, the term "methane-containing gas" refers to a gas that contains methane, such as biogas, natural gas, landfill gas, flue gas, marsh gas or mine gas are alternative terms. Methane-containing gas may be derived from any source, not being limited to the following group of possible origins: natural wetlands, rice fields, emission from animal production systems, fermentation, animal waste, degradation of organic waste, methane emissions, reclamation. Synonyms such as "methane-containing gases", "$CH_4$-containing gases" and "$CH_4$ containing gas" indicate an identical definition.

As used herein, the term "bamboo" refers to plant species belonging to the subfamily Bambusoideae of the Poaceae family, preferably defined as ligneous grass species. As used herein, "based on bamboo" or "bamboo-based" does not only refer to the bamboo plant, but is also indicative of materials or products made from bamboo, but is not limited to the following examples: furniture, scaffolding, palets, pots, planks, mats, cups, brushes, cutlery, multimedia accessories, toys, flooring, posts, paper, carton, clothing, pellets, briquettes, sports equipment, electronics covers, pipes, containers, baskets, chopsticks, window and door frames, musical instruments and weapons.

In particular embodiments, the method as described herein consists of the desulfurization of a methane-containing gas wherein the bamboo-based activated carbon used is generated from a supply product that consists of at least 50 wt % of bamboo. A consequence of this is that the bamboo-based activated carbon is used separately, or in combination with other substances that bring about filtering of one or more contaminants. The other substances that filter contaminants from the gas are used simultaneously with the bamboo-based activated carbon or at some other time in the purification process. If various purification steps take place, the methane-containing gas is brought into contact with the bamboo-based activated carbon and the other material simultaneously or alternately.

It was further established that if the raw material for producing bamboo-based activated carbon consists of at least 50 wt % of bamboo, this is advantageous for removal of sulfur from the methane-containing gas. The remaining percentage by weight preferably consists of alternative activated carbon supply products, or added products or molecules that possibly lead to an improvement of the action of the activated carbon in any way.

As used herein, the term "composition" refers to a composition of a mixture. Both quantitative and qualitative aspects of the composition are used for defining the composition.

As used herein, "wt %" refers to "percentage by weight" or to a definition identical to "percentage by mass" and is intended to quantify the relative amount by weight of a certain component and consequently the ratio of the weight of the component to the total weight. The sum total of all percentages by weight of a composition should give a result of 100%. Alternatively, percentage by weight is indicated as "fraction by weight", wherein the value varies from 0 to 1 inclusive. This value is equal to the percentage by weight divided by 100.

In particular embodiments, the method as described herein is characterized in that the pores of the activated carbon with which the methane-containing gas comes into contact form an alkaline environment. The composition of the bamboo-based activated carbon provides a natural alkaline environment, which improves the adsorption characteristics. Alkaline environment is formed before, during or after addition of the methane-containing gas. The alkaline environment is localized in the pores or extends on expansion over the complete mixture consisting of the bamboo-based activated carbon and the methane-containing gas.

As used herein, the term "alkaline" refers to the same definition as the term "basic". Alkaline is representative of an acid value (pH value) starting from 7 up to and including 14. The pH value of a solution is measured in various possible ways. pH indicators change color with increase or decrease of $H^+$ ions and their resultant color is indicative of a certain pH value. As an alternative, electrochemical reactions are carried out, wherein the voltage varies as a function of the pH. Another alternative is the pH established by titration.

In particular embodiments, the method for the desulfurization of methane-containing gases by bamboo activated carbon is applied in such a way that specific additional constituents are added individually or in combination to the activated carbon, such as $H_2O$ (water), NaOH (sodium hydroxide), $K_2CO_3$ (potassium carbonate), KI (potassium iodide), KOH (potassium hydroxide), CaO (calcium oxide), MgO (magnesium oxide), CuO (copper oxide) and/or MnO (manganese oxide). The inventors discovered that impregnation of bamboo-based activated carbon with said molecules has an advantageous activating effect on adsorption by giving rise to the formation of more alkaline active sites, which in their turn lead to the neutralization, oxidation and chemisorption of sulfur-containing compounds at room temperature and/or elevated temperature. In addition, the inventors found that said molecules are used as catalysts for removing pollutants by chemical degradation. In particular embodiments, combinations of the aforementioned molecules with the bamboo-based activated carbon are used in order to obtain an optimal composition for the adsorption of sulfur-containing compounds from methane-containing gases.

In particular embodiments, the method for the desulfurization of methane-containing gases by bamboo activated carbon is applied in such a way that specific amounts of additional constituents are added in precise amounts, individually or in combination, to the activated carbon. The inventors discovered that certain compositions bring about a further advantageous effect for adsorption of sulfur-containing compounds.

In particular embodiments, the method is used for the desulfurization of methane-containing gases that are defined as biogas, landfill gas, mine gas, marsh gas, or natural gas. The inventors discovered that bamboo-based activated carbon is ideally suited for the desulfurization of these gases. The use of these unpurified gases for further applications such as injection into the natural gas network or conversion to heat and/or electricity via a gas engine is hampered by the contaminating constituents of the methane-containing gas, which for safety reasons, reasons of restriction of emissions of environmentally harmful molecules into the atmosphere, or practical considerations, must be removed from the gas.

In particular embodiments, the method for the desulfurization of methane-containing gases by bamboo-based activated carbon is characterized by a high concentration of methane in the gas. The inventors discovered that the methane content of the gas varies and that the method described herein is particularly interesting when the gas preferably contains at least 10%, preferably at least 20%, preferably at least 40% and preferably at least 50% methane. The method is also used for gases wherein the methane content is higher than the above contents or is unknown at the start of the purification process.

In particular embodiments, the method for the desulfurization of methane-containing gases by bamboo-based activated carbon is characterized by a sulfur capacity of at least 50 wt % based on the initial fresh, unladen activated carbon.

The inventors discovered, unexpectedly, that these properties have a great influence on the method.

In general, a bamboo-based activated carbon that has a butane number of at least 20 is used for this method. The butane number is a measure of the pore volume of the activated carbon.

The method is also carried out by using an activated carbon that satisfies one of the parameters described. The inventors discovered that these parameters complement one another. A bamboo-based activated carbon that has a higher value for one parameter and a lower value for the other parameter still offers the desired desulfurization through mutual compensation of the parameters on execution of the method. Generally it is found that the higher the alkalinity and the higher the parameter of pore volume, the better the implementation of the method will be.

As used herein, the term "sulfur capacity" refers to a quantitative parameter defining the maximum capacity of a material to absorb sulfur.

As used herein, the term "internal surface" refers to a quantitative parameter that is indicative of the surface created by the pores. The internal surface of an amount of activated carbon is the total surface area of the same amount of activated carbon decreased by the external surface area of the same amount.

In particular embodiments, the method for the desulfurization of methane-containing gases is characterized in that the bamboo-based activated carbon is a reactivated carbon. The inventors discovered, unexpectedly, that reactivated carbon displays equivalent capacities to activated active carbon for accomplishing desulfurization. The reactivated carbon is reactivated according to any mechanism or sequence of steps.

As used herein, the term "reactivated carbon" refers to an activated carbon which, after saturation, has been recycled for subsequent application, which may or may not be identical to the first application carried out or preceding application. Reactivated carbon is used either for repeating a previous application in which the activated carbon was used or for carrying out another application.

In general, the reactivated carbon is used by itself. In particular embodiments the bamboo-based reactivated carbon is also mixed with fresh activated carbon that is produced at least partially from bamboo or from one or more other starting materials for making activated carbon. Additional constituents are also added to the bamboo-based reactivated carbon, which reinforce the sulfur purifying properties. These additional constituents are added during or after the reactivation steps and bring about an improvement of sulfur purifying properties.

In particular embodiments, the method for the desulfurization of methane-containing gases by bamboo-based activated carbon is characterized in that the content of hydrogen sulfide and other sulfur components in the methane-containing gas is reduced by at least 99% using fresh bamboo-based activated carbon relative to the same untreated gas before the desulfurization. The inventors discovered that larger reductions in sulfur concentrations are obtained by repeating the embodiments described.

In particular embodiments, bamboo-based activated carbon is used for the desulfurization of methane-containing gases.

It was also established that the use of bamboo-based activated carbon may be configured on the basis of the needs for required throughput of methane-containing gas, scale and velocity. The inventors additionally discovered that the degree of desulfurization of methane-containing gases is proportional to the amount of bamboo-based activated carbon.

In general, the method as described herein is used in fixed installations or mobile desulfurization units, whether or not forming part of a more extensive purification protocol for methane-containing gases. Use of the method as described herein means any use in an installation provided for one-time or repeated use.

In particular embodiments for the desulfurization of methane-containing gases by bamboo-based activated carbon, an installation is used that is able to carry out the method as described herein.

The inventors discovered that filtration installations that comprise bamboo-based activated carbon are extremely suitable for desulfurization of methane-containing gases, and in particular embodiments comprise better purification characteristics than activated carbon generated on the basis of other raw materials.

In general, all possible arrangements of the filtration installation aim at desulfurization of methane-containing gases that is as efficient as possible. Consequently, both stationary and mobile filtration installations are envisaged. The filtration installation is provided with a sufficient gas stream by any means. The flow of methane-containing gas or stopping thereof is achieved by manual or automated interventions. The installation may or may not contain one or more replaceable filters containing the bamboo-based activated carbon, possibly in combination with other substances having the function of purifying methane-containing gases.

In particular embodiments, the filtration installation additionally comprises overpressure or underpressure protection systems, and explosion protection systems. In further embodiments the filtration installation comprises measuring points at different levels for further monitoring of the quality of the purified gas.

EXAMPLES

Example 1

Characteristics of Bamboo-Based Activated Carbon Suitable for the Desulfurization of Methane-Containing Gases Sulfur content loading on the fresh activated carbon: ≥40%
BET: 900-1500 $m^2/g$
Hardness: 98%
Ash: 5 wt %-15 wt %
Water: 0 wt %-6 wt %
Iodine number: 950-1600 mg/g
Density: 250 g/L-500 g/L
Butane number: 20-37

Example 2

Desulfurization Procedure for Methane-Containing Gases by Bamboo-Based Activated Carbon Methane-containing gases typically comprise hydrogen sulfide concentrations varying from some tens of parts per million (ppm) to a few percent. On the alkaline internal surface of the activated carbon, hydrogen sulfide is split into $H^+$ and $HS^-$. The oxygen present in the methane-containing gas will, in combination with the water also present in the methane-containing gas, further oxidize these components to water and elemental sulfur. The elemental sulfur remains behind as the solid crystalline form within the pores of the activated carbon.

Example 3

Filtration Installation for the Desulfurization of Bamboo-Containing Gases by Bamboo-Based Activated Carbon A fixed or movable (mobile) filtration installation for purifying methane-containing gases, and which may also comprise bamboo-based activated carbon, typically has a connection through which the methane-containing gas enters, and a second connection through which the gas flows out. The connections are oriented in such a way that the methane-containing gas has maximum flow through the whole volume of active carbon.

A filtration installation further contains an opening through which the activated carbon can be fed into the filtration installation. The same opening, or another opening may be used for discharging the laden activated carbon from the filtration installation. The filtration installation may additionally be provided with overpressure or underpressure protection systems, explosion protection systems, and measuring points at different levels for further monitoring of the quality of the purified gas.

The invention claimed is:

1. A method for the desulfurization of methane-containing gases comprising contacting activated carbon with methane-containing gas, wherein the activated carbon is an activated carbon based on bamboo, characterized in that the activated carbon contains at least one of the following additional constituents: NaOH, $K_2CO_3$, CaO, MgO, and MnO.

2. The method as claimed in claim 1, characterized in that the activated carbon is generated from a composition consisting of at least 50 wt % of bamboo.

3. The method as claimed in claim 1, characterized in that pores of the activated carbon with which the methane-containing gas comes into contact form an alkaline environment.

4. The method as claimed in claim 1, characterized in that at least one of the additional constituents is present in the following amounts: 1.0 to 30.0% NaOH; 1.0 to 15.0% $K_2CO_3$; 1.0 to 10.0% CaO; 1.0 to 10.0% MgO; and/or 1.0 to 10.0% MnO.

5. The method as claimed in claim 1, characterized in that the methane-containing gas is a biogas, landfill gas, mine gas or natural gas.

6. The method as claimed in claim 1, characterized in that the methane-containing gas contains at least 10% methane.

7. The method as claimed in claim 1, characterized in that a saturated sulfur capacity of the activated carbon is at least 50 wt % relative to a fresh activated carbon.

8. The method as claimed in claim 1, characterized in that the activated carbon is a reactivated carbon.

9. The method as claimed in claim 1, characterized in that the sulfur content of the gas is decreased by at least 99% using fresh activated or reactivated carbon relative to untreated gas.

10. An installation arranged for the desulfurization of methane-containing gases by the method described in claim 1, comprising a filter that contains the activated carbon, wherein the filter accomplishes contact with methane-containing gas, wherein the activated carbon is an activated carbon based on bamboo, characterized in that the activated carbon contains at least one of the following additional constituents: NaOH, $K_2CO_3$, CaO, MgO, and MnO.

* * * * *